US008375943B2

(12) United States Patent
Shaffer et al.

(10) Patent No.: US 8,375,943 B2
(45) Date of Patent: Feb. 19, 2013

(54) PROCESS FOR TRANSIENT AND STEADY STATE DELIVERY OF BIOLOGICAL AGENTS TO THE LUNG VIA BREATHABLE LIQUIDS

(75) Inventors: Thomas H. Shaffer, Chadds Ford, PA (US); Marla R. Wolfson, Wyndmoor, PA (US)

(73) Assignee: Temple University—Of The Commonwealth System of Higher Education, Philadelphia, PA (US)

( * ) Notice: Subject to any disclaimer, the term of this patent is extended or adjusted under 35 U.S.C. 154(b) by 0 days.

(21) Appl. No.: 13/050,027

(22) Filed: Mar. 17, 2011

(65) Prior Publication Data

US 2011/0162646 A1 Jul. 7, 2011

Related U.S. Application Data

(63) Continuation of application No. 11/149,114, filed on Jun. 9, 2005, now Pat. No. 7,909,031.

(51) Int. Cl.

| | |
|---|---|
| *A61M 16/00* | (2006.01) |
| *A61M 16/10* | (2006.01) |
| *A61M 15/00* | (2006.01) |
| *A61M 11/00* | (2006.01) |

(52) U.S. Cl. ......... 128/203.25; 128/203.15; 128/203.12; 128/200.24; 128/200.14

(58) Field of Classification Search ............. 128/200.14, 128/200.21, 201.13, 202.26, 203.12, 203.16, 128/203.17, 203.26, 204.14, 204.17, 913, 128/203.15, 203.25; 424/673; 604/23–26
See application file for complete search history.

(56) References Cited

U.S. PATENT DOCUMENTS

| | | | | |
|---|---|---|---|---|
| 4,150,956 | A | 4/1979 | Vaseen | 58/48 |
| 4,232,665 | A | 11/1980 | Vaseen | 128/200.24 |
| 4,395,454 | A | 7/1983 | Baldwin | 428/290 |
| 5,277,176 | A | 1/1994 | Habashi et al. | 128/200.24 |
| 5,335,650 | A | 8/1994 | Shaffer et al. | 128/200.24 |
| 5,437,272 | A | 8/1995 | Fuhrman | 128/203.12 |
| 5,490,498 | A | 2/1996 | Faithfull et al. | 128/203.12 |
| 5,492,109 | A | 2/1996 | Hirschl et al. | 128/201.21 |
| 5,531,219 | A | 7/1996 | Rosenberg | 128/203.12 |
| 5,540,225 | A | 7/1996 | Schutt | 128/207.15 |
| 5,590,651 | A | 1/1997 | Shaffer et al. | 128/632 |
| 5,655,521 | A | 8/1997 | Faithfull et al. | 128/203.12 |
| 5,707,352 | A | 1/1998 | Sekins et al. | 604/56 |
| 5,788,665 | A | 8/1998 | Sekins | 604/19 |
| 5,829,428 | A | 11/1998 | Walters et al. | 128/200.24 |
| 5,853,003 | A | 12/1998 | Faithfull et al. | 128/203.12 |
| 5,927,273 | A | 7/1999 | Federowicz et al. | 128/200.24 |
| 6,012,453 | A | 1/2000 | Tsals et al. | 128/201.21 |
| 6,041,777 | A | 3/2000 | Faithfull et al. | 128/200.24 |
| 6,105,572 | A | 8/2000 | Shaffer et al. | 128/200.24 |
| 6,112,744 | A | 9/2000 | Högnelid | 128/200.24 |
| 6,116,235 | A | 9/2000 | Walters et al. | 128/200.24 |
| 6,119,687 | A | 9/2000 | Faithfull et al. | 128/203.12 |
| 6,242,472 | B1 | 6/2001 | Sekins et al. | 514/396 |
| 6,289,892 | B1 | 9/2001 | Faithfull et al. | 128/203.12 |
| 6,306,099 | B1 | 10/2001 | Morris | 600/529 |
| 6,694,977 | B1 | 2/2004 | Federowicz et al. | 128/204.18 |

(Continued)

*Primary Examiner* — Annette Dixon
(74) *Attorney, Agent, or Firm* — Drinker Biddle & Reath LLP

(57) ABSTRACT

The present invention includes a transient method of delivering a biological agent in a breathable liquid to a lung of a patient. The present invention includes a steady state method of delivering a biological agent in a breathable liquid to a lung of a patient. The steps of both the transient delivery method and the steady state delivery method can be controlled by a servo-control unit. A supplementary biological agent delivery step can be performed in both the transient method of delivering a biological agent and the steady state method of delivering a biological agent.

19 Claims, 5 Drawing Sheets

U.S. PATENT DOCUMENTS

| | | | |
|---|---|---|---|
| 7,909,031 B2 * | 3/2011 | Shaffer et al. | 128/203.25 |
| 2002/0153010 A1 | 10/2002 | Rozenberg et al. | 128/203.12 |
| 2004/0134486 A1 | 7/2004 | Robert et al. | 128/200.13 |
| 2005/0005936 A1 | 1/2005 | Wondka | 128/204.18 |

\* cited by examiner

PROCESS FOR TRANSIENT AND STEADY STATE DELIVERY OF BIOLOGICAL AGENTS TO THE LUNG VIA BREATHABLE LIQUIDS

CROSS-REFERENCE TO RELATED APPLICATIONS

This application is a continuation of application Ser. No. 11/149,114, filed Jun. 9, 2005, now U.S. Pat. No. 7,909,031. The entire disclosure of the aforementioned application is incorporated herein by reference.

TECHNICAL FIELD

The invention relates to administration of biological agents. Particularly, the invention relates to methods, process controls, systems, devices, and operating ranges for transient and steady state delivery of biological agents into the pulmonary system of a patient during liquid ventilation.

BACKGROUND OF THE INVENTION

Despite significant advances in respiratory care and reduction in mortality of patients with respiratory failure, morbidity persists, often resulting from iatrogenic mechanisms. In particular, preterm infants weighing less than 1500 grams experience significant acute and chronic respiratory complications. During this era of increasing multiple births secondary to infertility management, a greater number of very low birth weight and very preterm infants are being born, increasing the number of infants that experience these complications. Further, infants weighing less than 500 grams who survive the initial respiratory syndrome of prematurity, commonly (i.e., about 85% of the infants) experience significant chronic lung disease with neurodevelopmental delay. In this regard, these fragile infants represent an underserved population with respect to existing respiratory therapies. For this reason, alternative means to support pulmonary gas exchange while preserving lung structure and function are required.

To partially address this need, liquid assisted ventilation ("LAV") with breathable liquids such as perfluorochemical ("PFC") liquids has been investigated as an alternative respiratory modality. The biomedical application of PFC liquids has already been incorporated in clinical medicine for a number of different organ systems (i.e., intravascular PFC emulsions for volume expansion/oxygen carrying/angiography and intracavitary neat PFC liquid for image contrast enhancement or vitreous liquid replacement). As such, pure medical grade PFC liquids currently exist for LAV purposes.

Simplisitically, LAV utilizes a liquid to replace nitrogen gas as the carrier for oxygen and carbon dioxide. By definition, LAV is pulmonary gas exchange supported by tracheal instillation of a breathable liquid such as a PFC liquid. LAV techniques for the support of respiratory gas exchange include tidal liquid ventilation ("TLV"), PFC lavage, partial liquid ventilation ("PLV"), and aerosolized liquids. LAV techniques differ with respect to methodology as well as the impact of the physiochemical profile of the PFC liquid.

Figure 1:
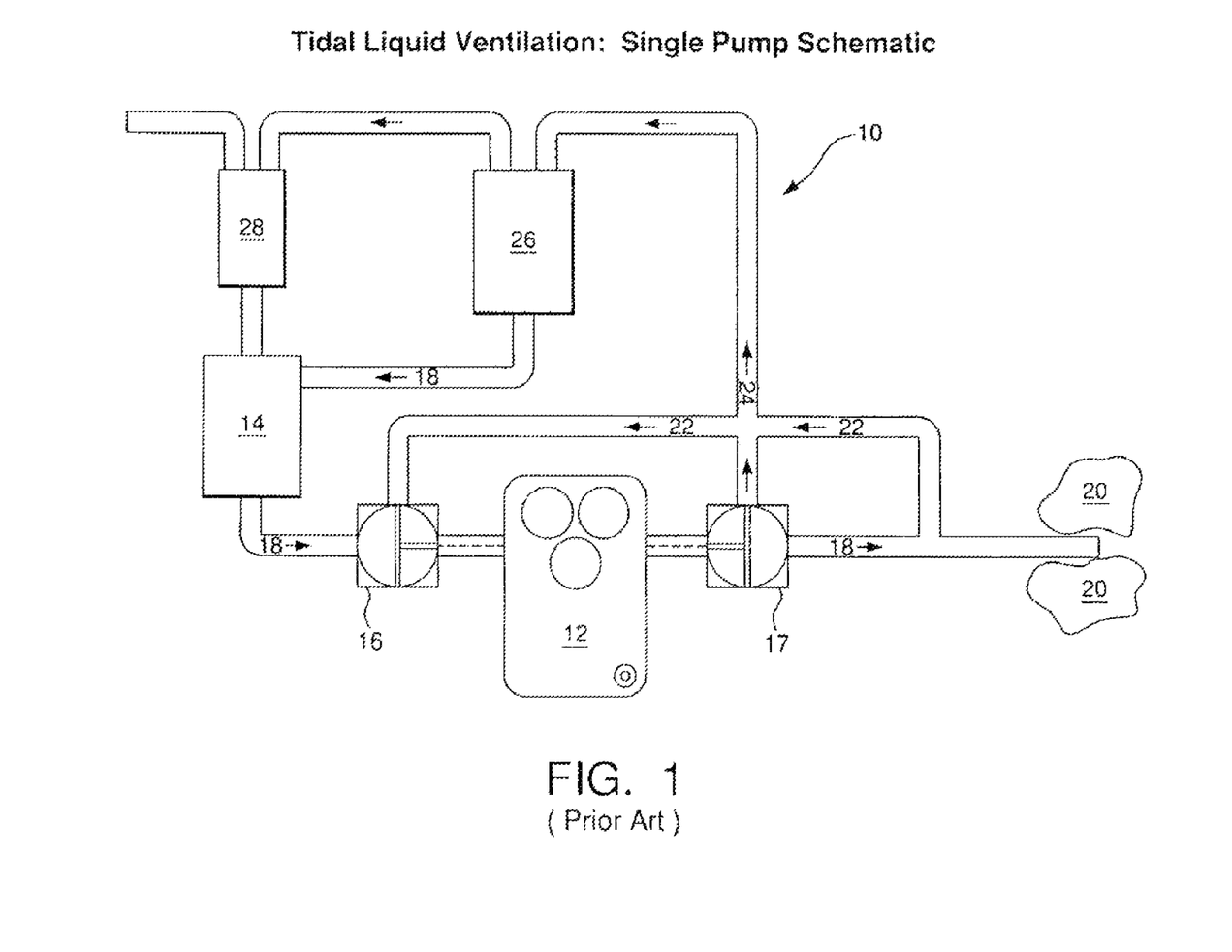
FIG. 1 is a schematic of a prior art single pump liquid ventilation system.

A single pump ventilatory system 10 as shown in FIG. 1 can be used for performing the various LAV techniques. For example, the ventilatory system 10 can be used for TLV. During inspiration, a pump 12 is used to pump a warmed and oxygenated PFC liquid from a liquid reservoir 14 through an inspiratory valve 16 in direction 18. The PFC liquid is pumped into lungs 20. During expiration, the PFC liquid is actively pumped out of the lungs 20 (with passive assistance from the naturally occurring lung recoil) in a direction 22. The PFC liquid is then pumped in a direction 24 through a gas exchange filter 26, and if necessary a conditioner 28, before being pumped back to the liquid reservoir 14. In the gas exchange filter 26, carbon dioxide is scrubbed out of the PFC liquid and oxygen is dissolved into the liquid. Control of the inspiration valve 16 and an expiration valve 17 allows recirculation of the PFC liquid in the system 10, without the liquid being delivered to the lungs 20. This recirculation may be necessary if excess amounts of carbon dioxide or insufficient amounts of oxygen are present in the liquid.

Using the system 10, the TLV process is initiated by instilling PFC liquid into the lung of a patient (which is initially filled with gas) while gently manipulating the thorax to assist removal of resident gas volumes into the delivery system. Because gas is transported in dissolved form, the gas-liquid interface at the alveolar surface is eliminated, there are no audible breathing sounds, and inflation pressures are minimized. There is no free gas in the lung and the liquid volumes in the lung and ventilator are monitored and controlled to maintain effective gas exchange. In this way, substantially all gas-liquid interfacial tension is eliminated and the lung is provided maximal protection from inflation pressures as lung volume is recruited, compliance is increased, and inflation pressures and pulmonary barotraumas are reduced.

Figure 2:
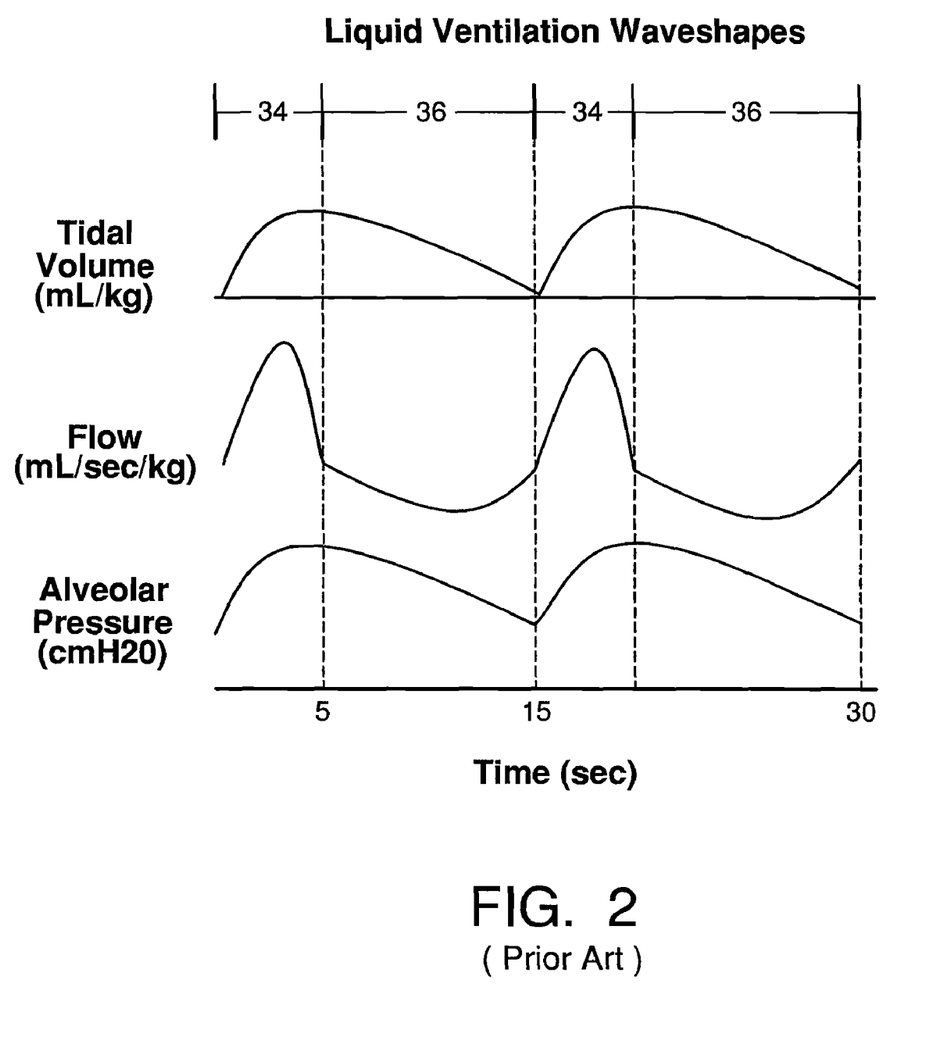
FIG. 2 is a graph showing tidal volume, flow, and alveolar pressure of a typical patient undergoing liquid lung ventilation.

The control of the ventilatory system can be achieved by cycling the liquid using a mechanical ventilator, which can include manually controlled flow-assist pneumatic systems, roller pumps with pneumatic/liquid/electronic controls, and gravity driven and modified ExtraCorporeal Membrane Oxygenation ("ECMO") circuits. Current control strategies include constant pressure or constant flow or time-cycling with pressure (system, airway, or alveolar) and/or volume (lung volume, tidal volume) limitations. The current approaches may provide for a servo-controlled system based on feedback of ventilatory parameters such as those shown in FIG. 2 where values for inspiration period 34 and expiration period 36 are obtained. However, the current approaches do not provide for a delivery system with a microprocessor or servo-control unit that maintains gas exchange, optimizes lung function, minimizes ventilation pressures, and optimally delivers a biological agent to the patient.

In an effort to optimize delivery of breathable liquids in a ventilatory system, Tidal liquid ventilation algorithms that address optimum frequency (3-8 breaths/minute), tidal volume (about 15 ml/kg) and inspiratory:expiratory timing (1:2 or 1:3) have been developed. Those algorithms are run as a control strategy to maintain adequate $CO_2$ elimination (up to 4× steady state values), minimize resistive pressures and expiratory flow limitations associated with moving the relatively more dense and viscous respiratory medium, and overcome diffusional dead space associated with $CO_2$ diffusivity in a liquid respiratory media. The control strategy allows for proximal airway pressures to be rapidly dissipated through the bronchopulmonary tree during TLV such that alveolar pressures are markedly lower than airway pressures. As a result, pulmonary debris (i.e., exudates, meconium, mucous) is readily moved by tidal PFC volumes and cleared by the TLV filtering systems.

The ventilation system shown in FIG. 1 can also be used for partial liquid ventilation ("PLV"). PLV can be performed by filling and maintaining the lung with a functional residual capacity of PFC liquid while mechanical gas ventilation is performed. In this way, PLV is similar to TLV as it utilizes the alveolar recruitment capabilities of a low surface tension liquid to establish an adequate functional residual capacity (i.e., lung volume after a normal expiration) in a surfactant deficient, or impaired lung. The PFC liquid is oxygenated and $CO_2$ is exchanged in the lung through mechanical gas ventilation.

The technical aspect of instilling PFC liquid and adjustment of the gas ventilator are known in the art, but effective ventilation of a lung which is partly filled with liquid and partly filled with gas is more challenging since there are many unknowns with respect to the distribution of PFC liquid in the lung, oxygen and carbon dioxide saturation of resident PFC, continually changing lung mechanics, evaporative loss of PFC, and changing volumes of gas and PFC lung volumes. Thus, there is a need for constant monitoring and adjustment of ventilatory parameters.

Although various LAV techniques are used in treating pulmonary disorders, what is still needed is a method for effectively treating pulmonary disorders with breathable liquids and biological agents. In particular, what is needed is a method for treating pulmonary disorders with breathable liquids and biological agents, wherein the method is practiced using a microprocessor or a servo-control unit to control the delivery system so as to maintain gas exchange, optimize lung function, minimize ventilation pressures, and optimally deliver the biological agents.

SUMMARY OF THE INVENTION

One embodiment of the present invention includes a transient method of delivering a biological agent to a lung of a patient during liquid ventilation. The transient method includes establishing a baseline ventilation pattern in the patient. The baseline ventilation pattern is established while a breathable liquid is administered to the patient's lung through a delivery system. The baseline ventilation pattern includes a baseline lung volume, a baseline tidal volume, and a baseline inspiratory time of the baseline tidal volume. After the baseline ventilation pattern is established, additional breathable liquid is added to the lung by way of the delivery system to increase lung volume above the baseline lung volume. In a subsequent breath, the patient's lung is then allowed to reach mid-tidal volume. At or about mid-tidal volume, a biological agent is introduced into the delivery system. The tidal volume in the lung is then increased above the baseline tidal volume by administering additional breathable liquids. The inspiratory time in the lung is increased above the baseline inspiratory time of the baseline tidal volume by increasing the residence time of the breathable liquid in the lung. The ventilation pattern is then returned to the baseline ventilation pattern.

Another embodiment of the present invention includes a steady state method of delivering a biological agent to a lung of a patient during liquid ventilation. The steady state method includes mixing the biological agent in a delivery system with a volume of breathable liquid that is greater than or equal to an initial filling volume of the lung. The mixing creates a substantially homogeneous therapeutic mixture. The lung of the patient is filled with the therapeutic mixture. The therapeutic mixture is circulated through the lung and the delivery system. Additional biological agents are injected into the delivery system as needed to maintain a substantially uniform concentration of the biological agent in the breathable liquid.

Both the transient delivery method of delivering a biological agent during liquid ventilation and the steady state delivery method of delivering a biological agent during liquid ventilation can be practiced with a delivery system controlled by a servo-control unit.

A supplemental step of delivering of a biological agent during liquid ventilation can be performed in conjunction with the transient method of delivering a biological agent and the steady state method of delivering a biological agent.

DETAILED DESCRIPTION OF THE INVENTION

One embodiment of the present invention includes a transient method of delivering a biological agent ("BA") in a breathable liquid to a lung of a patient ("transient BA delivery method"). Another embodiment of the present invention includes a steady state method of delivering a BA in a breathable liquid to a lung of a patient ("steady state BA delivery method"). A supplemental step of delivering a BA in a breathable liquid to a lung of a patient ("supplemental BA delivery") can be performed in conjunction with both the transient BA delivery method and the steady state BA delivery method.

As used herein, the target of the BA delivery is "a lung of a patient". This phrase should not be construed to limit the present invention from being practiced on both lungs of the patient. Also, as used herein, the articles "a" and "an" refer to one or to more than one (i.e. to at least one) of the grammatical object of the article. By way of example, "an element" means one element or more than one element.

As used herein, biological agent or BA is defined to include, but not be limited to, a diagnostic agent, a contrast agent, a surfactant, a steroid, an antibiotic agent, an anti-cancer agent, a chemotherapeutic agent, a chemotactic agent, a vasoconstrictor, a bronchoconstrictor, a vasodialator, a bronchodialator, a toxin, an antibody-linked radionuclide, and combinations thereof.

In one embodiment, the biological agent is a solid. The solid biological agent can be dissolved or suspended in the breathable liquid.

In another embodiment, the biological agent is a liquid.

In yet another embodiment, the biological agent is a gas other than oxygen. Preferably, the gas is a therapeutic gas. For example, the gaseous biological agent can be nitric oxide, nitrous oxide, anesthetic agents (e.g., chloroform, bromoform), and hydrogen sulfide. Additionally, the gas can be in the form of microbubbles in the breathable liquid, allowing the gas to act as a contrasting agent.

The amount of biological agent to be administered to a patient depends on several factors including the type of biological agent or agents to be administered, the method of delivery, the ailments or reasons for administering the biological agent or agents, the age of the patient, the gender of the patient, the weight of the patient, and the like.

As used herein, "breathable liquid" is defined as a liquid that can be used in place of or in conjunction with air to deliver oxygen to and remove carbon dioxide from a pulmonary system of a patient. The process of gravity-assisted and/or mechanically-assisted passing of the breathable liquid through at least a portion of the patient's pulmonary pathways is defined herein as "liquid ventilation."

The breathable liquid can be a perfluorochemical, silicone, saline, vegetable oil, and the like. Preferably, the breathable liquid is a perfluorocarbon ("PFC") liquid.

Different breathable liquids have different physiochemical properties such as kinematic viscosity, spreading coefficients and $CO_2$ solubility causing diverse patterns of distribution and elimination. For example, a liquid with higher kinematic viscosity tends to distribute less homogeneously but also resists redistribution over time. Thus, such a liquid maintains greater contact with the inspired gas and eliminates relatively faster than a liquid of lower kinematic viscosity and comparable vapor pressure. Liquids of higher vapor pressure will volatize into the expired gas more rapidly than lower vapor pressure liquids.

Because of its favorable physiochemical properties, a PFC liquid is the preferred breathable liquid. PFC liquids are clear, colorless, odorless, non-conducting, and nonflammable. PFC liquids are twice as dense as water, and are capable of dissolving large amounts of physiologically important gases (mainly oxygen and carbon dioxide). PFC liquids are generally chemically stable compounds that are not metabolized in body tissues. PFC liquids are biologically and chemically inert. Also, they possess a high respiratory gas solubility (up to 50 and 210 ml of gas/100 ml liquid for oxygen and carbon dioxide, respectively) and a low surface tension (15 dynes/$cm^2$).

The physiochemical attributes of PFC liquids support their application to the pulmonary system. PFC liquids are an excellent medium to carry respiratory gases. PFC liquids at one atmosphere of pressure can carry about 20 times more oxygen than saline can carry and can carry up to about 3 times more oxygen than is present in ambient air. Because of the chemical makeup of PFC liquids (e.g., low surface tension), they can spread uniformly and quickly throughout the lungs, thus ensuring rapid delivery of the liquid to the alveoli. In addition, PFC liquids exhibit anti-oxidative properties and anti-inflammatory characteristics.

The combination of the physiochemical properties of the PFC liquid and the biophysical effects of the liquid on lung mechanics support physiologic responses. Due to relatively low surface tension, high respiratory gas solubility and high spreading coefficients, PFC liquid instillation replaces the gas-liquid interface with a liquid-liquid interface at the lung surface while supporting an adequate alveolar reservoir for pulmonary gas exchange. In turn, high surface tension at the gas-liquid interface is eliminated and interfacial tension is reduced. Because transmural pressures across the alveolar-capillary membrane are more evenly matched, pulmonary blood flow is more homogeneous in the liquid as compared to a gas filled lung.

Because of the unique characteristics of PFC liquids, there are many potential benefits that can be gained from its administration to a patient's lung. These benefits, some of which are noted above, include: improving gas exchange in the lung, opening an atelectatic area in the lung by recruitment thereby increasing total lung capacity, opening a collapsed alveoli by acting as a surfactant, decreasing the chance of oxygen toxicity in the lung, decreasing inflammation in the lung, and increasing pulmonary blood flow to injured lung areas creating better oxygenation, enhancing pulmonary delivery of contrast media to the pulmonary system.

These same properties that make PFC liquids attractive for liquid ventilation lend to their potential for serving as a delivery vehicle for delivering a BA to a patient's lung. The high respiratory gas solubility supports high gas exchange, allowing better delivery of the BA. The low surface tension and ability to recruit lung volume allow for BA distribution to under ventilated lung regions. Additionally, the inert nature of the PFC liquid precludes any BA-vehicle (i.e., PFC liquid) interactions. However, because little is soluble in PFC liquids, the BA when in solid form, typically in the form of nanocrystals, must be suspended in the PFC liquids.

When BAs in PFC liquid are delivered during tidal liquid ventilation, it is possible to control the delivery rate, the time of injection, and the total amount of BA delivered to the target site, i.e., the lung. To do so, one embodiment of the present invention includes synchronization of liquid ventilation technology with delivery of BAs. Synchronization provides for a distribution of the BA in the lung that is more homogenous than the prior attempts to utilize PFC liquids as a delivery vehicle, which relied on bulk flow delivery of the BAs. In turn, the present invention provides for a more effective treatment of the patient.

The delivery system for the BA can be either an open-loop system or a closed-loop system. An open loop system typically allows gas exchange in the lungs by a combination of respiratory gas (containing oxygen) and a breathable liquid having oxygen solubilized in it. Open loop systems are generally employed with partial liquid ventilation. In contrast, gas exchange in the lungs is performed in a closed loop system almost entirely by a breathable liquid having oxygen solubilized in it.

Known liquid ventilation systems, such as disclosed in U.S. Pat. No. 6,105,572 Shaffer et al., can provide the basis for the delivery systems of the present invention. The delivery system of the present invention can include a liquid reservoir, a pump, a piping network including valves, a gas exchange filter and/or oxygenantors, a condenser, and an endotracheal tube.

Warmed and oxygenated breathable liquid is housed in the liquid reservoir. The liquid reservoir is preferably constructed of and/or lined with a material that is compatible with the breathable liquid. For example, when the breathable liquid is a PFC liquid, the liquid reservoir can be constructed of and/or lined with urethane, viton and the like.

The breathable liquid is conveyed to and from the liquid reservoir and to and from the patient's lung by way of a pump. In particular, during inspiration, the pump conveys a warmed and oxygenated breathable liquid from the reservoir to the patient's lung and during expiration, actively pumps the breathable liquid out of the lung (with passive assistance from the naturally occurring lung recoil). The pump can be a piston pump, a roller pump, or any other type of pump capable of fulfilling the required function. Further, the delivery system can include multiple pumps for conveying the breathable liquid through the system.

Once the breathable liquid is pumped from the lung, it is passed through a gas exchange filter. The gas exchange filter scrubs out carbon dioxide of the breathable liquid and dissolves oxygen into the liquid. The filters, which can be obtained from numerous commercial sources, are selected based upon compatibility with the breathable liquids and the BAs of the invention. In a preferred embodiment, a filter equivalent to a conventional blood filter is used.

For further oxygenation, the breathable liquid can be passed through an oxygenator. The primary function of the oxygenator is to maintain the quantity of oxygen in the breathable liquid at or about the level of saturation. Any type of oxygenator capable of fulfilling the required function can be used.

A heating system can be coupled to the oxygenator and/or the gas filter to warm the breathable liquid to at or about the body temperature of the patient. Initially, the heating system is run continuously until a target temperature (e.g., patient's internal body temperature) is reached. Once the target temperature is reached, the heating system is operated only to compensate for thermal losses and maintaining the breathable liquid at this target temperature.

The breathable liquid is also passed through a condenser. The condenser condenses evaporated breathable liquid and returns it in the form of a liquid to the gas exchange filter and/or the oxygenator.

The breathable liquid is conveyed, both during inspiration and expiration, through a piping network. The material for the piping network should be selected based upon its compatibility with the breathable liquid being conveyed. For example, where the breathable liquid is a PFC liquid, the material can be urethane, viton and the like. The size or diameter and the length of the piping can be selected based upon the volume of breathable liquid that is being delivered to the patient and the location of the patient relative to the delivery system.

The piping network also includes valves that can be opened and closed to control flow. For example, the valves can be opened and closed such that the breathable liquid is not delivered to the lung of the patient but rather recirculated in the system. This recirculation may be necessary if excess amounts of carbon dioxide or insufficient amounts of oxygen are present in the breathable liquid.

The piping network can connect to communicate with the lung of the patient through an endotracheal tube. The connection can include a connector, which preferably is comprised of a material and configuration known to those of skill in the art such as a T or Y connector.

One end of the endotracheal tube connected to the piping network, with the other end inserted into the trachea of the patient. This configuration provides for the delivery of the inspired breathable liquid to and the removal of the expired breathable liquid from the patient's lung. The endotracheal tube preferably comprises a conduit made of polymer tubing of a material and configuration known to those of skill in the art.

Beyond the features of the known liquid ventilation systems, the delivery system of the present invention can include a BA injector unit and a sonicating or vibration/agitation unit. The function of the BA injector is to introduce the BA to the delivery system. The location of the BA injector in the delivery system can vary. For example, for the steady state BA delivery method, the BA injector is preferably coupled with the liquid reservoir so that the BA is injected directly into the breathable liquid housed in the reservoir. For the transient BA delivery method, the BA injector is preferably at a location in the delivery system that is closer to the patient's lungs such as being coupled with the endotracheal tube. In addition, the injector is preferably oriented perpendicular to the flow of the breathable liquid. A perpendicular orientation allows for greater mixing of the BA with the breathable liquid.

The injector can include a manual override option. The manual override provides both safety (e.g., terminating the injection if a patient has an adverse reaction to the BA) and flexibility of operation (e.g., allowing medical personnel to give a small dose injection without having to program the entire delivery system).

The injector preferably is coupled with a sonicator. A sonicator is a device that emits high frequency sound waves, which when coupled with the injector would provide for greater suspension of the BA in the breathable liquid over longer period of time. The coupling must be such that the injected BA and the breathable liquid are exposed to the high frequency sound waves.

Alternatively, a vibratory unit, an ultrasonic unit, or another similar type unit can be coupled with the injector to provide for greater suspension of the BA in the breathable liquid over a longer period of time. A vibratory unit provides for greater suspension by vibrating the BA and the breathable liquid. An ultrasonic unit provides for greater suspension by exposing the BA and the breathable liquid to high frequency vibrations.

Each of these features, as well as any additional features, are preferably controlled by a servo-control unit. As used herein, a "servo-control unit" includes a microprocessor, a computer programming unit ("CPU") or any other programmable device where algorithms can be entered to control the features of the delivery system to optimize BA delivery to the patient's lung. Servo-control of the BA delivery methods of the present invention allows the methods to be carried out in a timed fashion based on algorithms programmed by the treating medical professional. In addition, with the servo-control unit, the delivery system can measure physiological parameters in the patient (e.g., identifying the exact moment in which the patient's lung reaches mid-tidal volume in a breath) and then use these measurements as feedback for servo-control of ventilatory parameters to optimize delivery of the uptake of the BA by the patient's lung.

In addition, servo-control of the methods allows the medical personnel to have flexibility in programming delivery methods to most effectively treat the patient. The flexibility allows the medical personnel to control the BA delivery based on factors such as maintaining gas exchange, optimizing lung function, minimizing ventilation pressures and optimally delivering BA to the pulmonary system. For clinical applications in patients with lung disease, such safe and optimum control is critical, especially in the intensive care setting.

Servo-control of the BA delivery methods of the present invention also reduces the cost of treating a patient. Respiratory care with liquid ventilation is intrinsically expensive because of, among other reasons, the high cost of breathable liquids and the high cost of BAs. The control of the BA delivery methods of the present invention by a microprocessor or servo-control unit optimizes the delivery of the BAs and the breathable liquid, thereby limiting the waste of these high cost items.

In addition, the closed-loop embodiment of the BA delivery systems of the present invention can also reduce the cost of treating a patient. The closed-loop system reduces the amount of BA and the amount of breathable liquid lost during ventilation (breathable liquids are generally not metabolized during treatment, rather their losses are mostly attributable to system leakage and evaporation).

The transient BA delivery method includes the step of establishing a baseline ventilation pattern in the patient. The baseline ventilation pattern is established by stabilizing the ventilation of a patient undergoing liquid ventilation. Stabilization can occur by adjusting the volume and/or flow of the breathable liquid to the patient.

As used herein, the baseline ventilation pattern is a series of ventilatory parameters that are optimized in a particular patient prior to subsequent steps in the transient BA delivery method. The baseline ventilation pattern includes a baseline lung volume, a baseline tidal volume, and a baseline inspiratory time of the baseline tidal volume. The baseline ventilation pattern can also include a baseline expiratory time, a baseline inspiratory:expiratory timing ratio, a baseline breathing rate, a baseline inspiratory flow rate, a baseline expiratory flow rate, and a baseline alveolar pressure.

"Tidal volume" is defined as the amount of breathable liquid taken into the lungs in a single breath. An optimal baseline tidal volume is generally from about 10 to about 20 ml/kg.

"Inspiratory time" is defined as the amount of time required for the inspiration of a single breath. An optimal baseline inspiratory time is from about 3 to about 7 seconds. Preferably, the optimal baseline inspiratory time is about 5 seconds.

"Expiratory time" is defined as the amount of time required for the expiration of a single breath. An optimal baseline expiratory time is from about 8 to about 15 seconds. Preferably, the optimal baseline expiratory time is about 10 seconds.

"Inspiratory:expiratory timing ratio" is defined as a ratio of the inspiratory time and the expiratory time. An optimal baseline inspiratory:expiratory timing ratio value is generally from about 1:2 to about 1:3.

"Breathing rate" is defined as the amount of breathes taken over a set period of time. An optimal baseline breathing rate is from about 3 to about 8 breaths per minute (br/min).

"Inspiratory flow rate" is defined as the rate at which breathable liquid is inspired. An optimal baseline inspiratory flow rate is from about 200 to about 280 ml/sec/kg. Preferably, the optimal baseline inspiratory flow rate is about 240 ml/sec/kg.

"Expiratory flow rate" is defined as the rate at which breathable liquid is expired. An optimal baseline expiratory flow rate is from about 20 to about 60 ml/sec/kg. Preferably, the optimal baseline expiratory flow rate is about 40 ml/sec/kg.

"Alveolar pressure" is defined as the pressure exerted on the alveoli of the lungs during inspiration and expiration. An optimal baseline alveolar pressure is about 10 $cmH_2O$ for inpiratory pressure and 3 $cmH_2O$ for expiratory pressure.

After the baseline ventilation pattern is established, the patient's lung volume is increased by adding additional breathable liquid into the lung during inspiration. Preferably, the increase in lung volume is no more than about 33% greater than the baseline lung volume; more preferably from about 5% to about 30% greater than the baseline lung volume; and most preferably about 25% greater than the baseline lung volume.

Preferably, the increase in patient's lung volume is performed in a step-wise manner, i.e., the additional breathable liquid is added to the lungs over several breaths. The step-wise increase of the lung volume is appropriate, for example, when administering a BA such as a chemotherapeutic drug for cancer treatment where immediacy of the BA delivery is not a factor.

Alternatively, the increase in lung volume can be performed by adding additional breathable liquid during just one breath. Increasing lung volume in just one breath is advantageous, for example, when administering a life saving BA where immediacy of the BA delivery is a factor.

The increase in lung volume increases alveolar surface area in the patient's lung and decreases thickness of the alveolar capillary interface. These changes, as defined by the Fick principle, prime the lung for an increase in the diffusion rate of the BA across the tissues of the lung. Thus, the increase in lung volume facilitates rapid exchange of the BA across the alveolar capillary membrane into the interstitium, parenchyma, and circulation once the BA is introduced.

Preferably, the increase in lung volume is automated, by, for example, being controlled by a servo-control unit. Automation allows for the programming of a precise increase in lung volume (e.g., a 25% increase). Automation also can ensure that the breathable liquid is only added during the patient's inspiration phase of breathing. Such automation becomes critical when the lung increase is performed in a step-wise manner where addition of the breathable liquid must be started and stop in accordance with the inspiration and expiration breathing phases. If attempts are made to add breathable liquid during expiration, breathing complications could occur.

After the patient's lung volume has been increased, the lung is then allowed, in a subsequent breath, to reach at or about mid-tidal volume. At or about mid-tidal volume, a BA is introduced into the delivery system. Preferably, the BA is introduced at plus or minus 10% of the mid-tidal volume; more preferably at plus or minus 5% of the mid-tidal volume; and most preferably at the mid-tidal volume. Maximum flow conditions in the delivery system exist at the mid-tidal volume, thus introduction of the BA at or about mid-tidal volume allows for effective mixing of the BA and the breathable liquid, which, in turn, increases dissolution of the BA and increases uniformity of the BA concentration in the breathable liquid. The maximum flow conditions also allow for effective convective transport of the BA.

Depending on the amount of BA to be administered, the BA can be introduced into the delivery system in a single breath or over multiple breaths. The BA can be introduced using a BA injector.

Preferably, introduction of the biological agent into the delivery system is automated by, for example, being introduced with a BA injector linked with a servo-control unit. With an automated BA injection, the mixing of the BA and the breathable liquid increased because the BA can be introduced into the delivery system substantially at the mid-tidal volume (i.e., at maximum flow conditions). The automated system can be programmed to measure when the lung is at mid-tidal volume and then, relying on this measurement, introduce the BA at or about the mid-tidal volume.

The amount and timing of BA delivery can vary. These variations can be programmed into the servo-control unit such that the delivery of the BA to a particular patient for a particular treatment regimen is optimized.

After injection of the biological agent, tidal volume and inspiratory time in the lung are increased. The tidal volume is increased above the baseline tidal volume. The inspiratory time is increased above the baseline inspiratory time of the baseline tidal volume. The tidal volume in the lung can be increased above the baseline tidal volume by administering greater volumes of breathable liquids. Preferably, the increased tidal volume is no more than about 20% greater than the baseline tidal volume. The inspiratory time in the lung is increased above the baseline inspiratory time of the baseline tidal volume by increasing the residence time of the breathable liquid in the lung. Preferably, the increased inspiratory time is no more than about 66% greater than the baseline tidal volume.

The length of time that the increased tidal volume and increased inspiratory time are maintained is dependent on among other things, the pharmacokinetics of the BA being administered to the patient. Preferably, the increased tidal volume and increased inspiratory time are maintained from about 1 breath to about 15 breaths of the patient and more preferably from about 5 breaths to about 10 breaths of the patient.

The increase in tidal volume and the increase in inspiratory time is preferably automated, by, for example, being controlled by a servo-control unit. Automation of the increase allows the treating medical professional to program, among other things, the amount of the increases, the manner in which the increases are performed, and the duration of the increases. For example, the servo-control unit can calculate the amount of the increases and the duration of the increases simply from the medical professional's input of the BA being administered. The servo-control unit could then carry out the increases based on these calculations.

The ventilation pattern is then returned to the baseline ventilation pattern by adjusting the flow, concentration, etc. of the breathable liquid being delivered to the lung. Again, as with the previous steps of the transient BA delivery method, the return to the baseline ventilation pattern is preferably automated.

Figure 3:
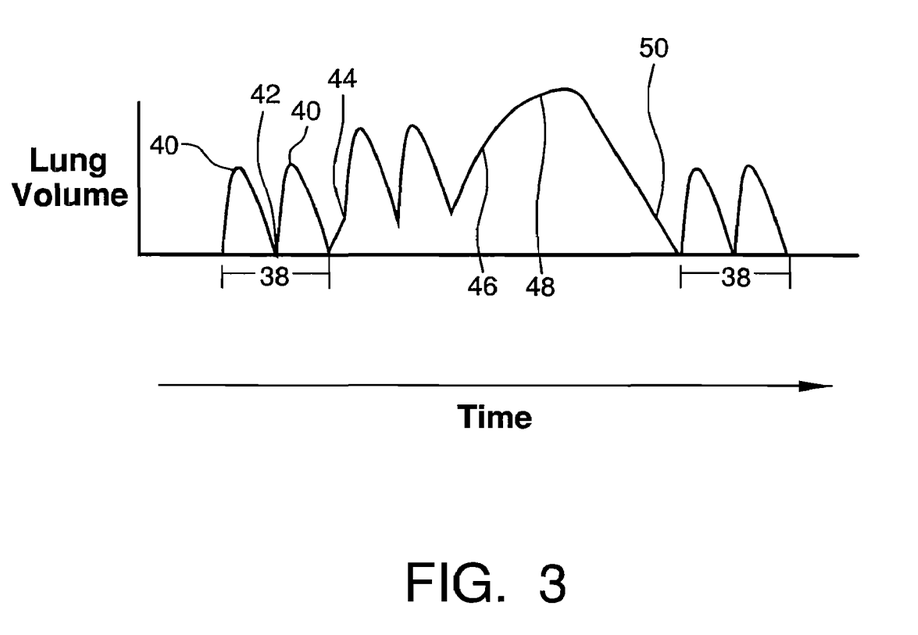
FIG. 3 is a graph showing lung volume over time during the practice of a method for transient delivery of a biological agent in a breathable liquid.

FIG. 3 graphically depicts a patient's lung volume over time during the transient BA delivery method. The peaks 40 represent the transition between inspiration of a breath and expiration of the breath. The valleys 42 represent the transition between expiration of the breath and inspiration of the next breath. The initial step of establishing a baseline ventilation pattern in the patient is represented by time interval 38.

Following the establishment of a baseline ventilation pattern, the first step of the method is to increase the patient's lung volume. The increase in lung volume is depicted by time point 44.

After the lung volume is increased, the second step of the method is to introduce the BA to the delivery system by injection or by other known means at or about mid-tidal volume, which is marked as 46 in FIG. 3.

After the BA has been introduced, the third step, corresponding to 48 in FIG. 3, includes increasing the tidal volume in the patient's lung and increasing the inspiratory time of the tidal volume. The increase in tidal volume and the increase in inspiratory time can be performed as separate steps, but are preferably performed together. The final step, corresponding to 50 in FIG. 3, is to return the ventilation pattern to the baseline ventilation pattern, which includes decreasing the lung volume, decreasing the tidal volume, and decreasing the inspiratory time.

In order to maintain therapeutic concentrations of the BA following the transient delivery, a supplemental amount of BA can be added to the delivery system. The supplemental BA is preferably added to the delivery system at the rate at which the BA is metabolized by the patient or lost to the target organ systems. The rate of metabolization or loss is generally dictated by the pharmacokinetics and excretion of the particular BA which is being administered to the lung of the patient.

The supplemental delivery may also be necessary to provide concentrations of the BA at levels that cannot be attained by the transient delivery method alone e.g., concentration levels that cannot be attained from merely one injection (e.g., concentrations of solid BA in the breathable liquid are too high, the BA may precipitate out). The steps of the supplemental BA delivery are substantially the same as the steps of the transient BA delivery method described above.

Figure 4A:
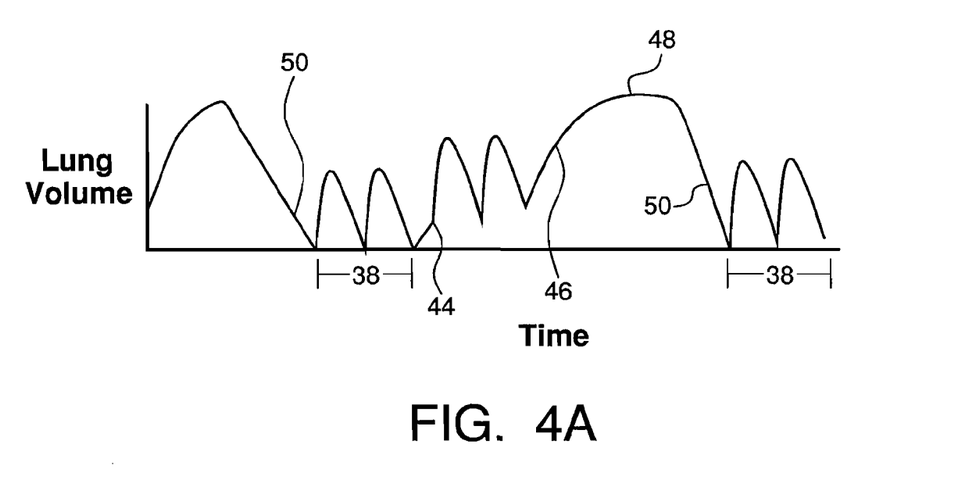
FIG. 4A is a graph showing lung volume over time during the practice of a supplemental delivery of a biological agent in a breathable liquid after the transient biological agent delivery method was performed.

FIG. 4A graphically depicts a patient's lung volume versus time during the supplemental BA delivery after the transient BA delivery method has been performed. After the final step, corresponding to 50, of the transient BA delivery method, the ventilation pattern is returned to the baseline ventilation pattern, as represented by time interval 38. The baseline ventilation pattern can then be maintained for any period of time. As illustrated, the baseline ventilation pattern is maintained for two breaths. During inspiration of the third breath, the patient's lung volume is increased as depicted by time point 44. The subsequent steps of introducing the BA to the delivery system at or about mid-tidal volume (marked as 46 in FIG. 4A), and returning the ventilation pattern to the baseline (marked as 50 in FIG. 4A) are then performed as described for the transient BA delivery method. The supplemental BA delivery can be performed as many times as necessary to delivery or maintain the desired concentration of the BA in the patient's lung.

Figure 4B:
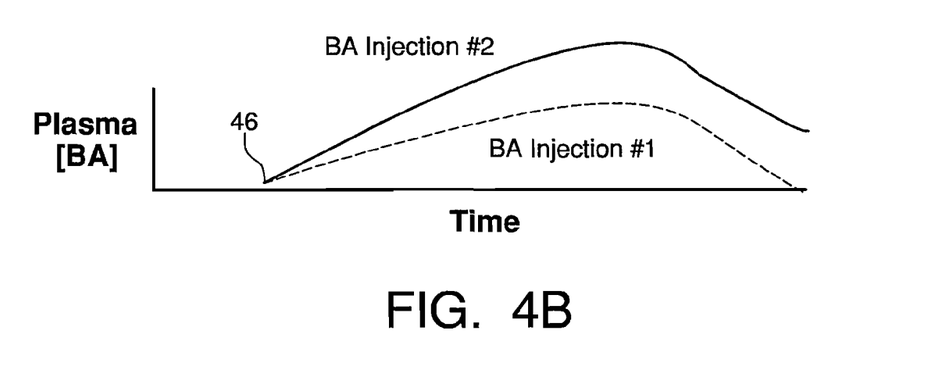
FIG. 4B is a graph showing the effect the injection concentration of the biological agent has on the concentration of the biological agent in the plasma.

FIG. 4B shows the effect the quantity of BA injected has on the concentration of the BA in the breathable liquid that is delivered to the patient's lung. The graph compares an Injection #1 and an Injection #2 as if the injections were made in isolation of one another at time point 46. The quantity of BA injected in Injection #1 is less than the quantity of BA injected in Injection #2. As a result, the concentration of the BA in the breathable liquid from Injection #1 is less than the concentration of BA in the breathable liquid from Injection #2. In both Injection #1 and Injection #2, the concentration of the BA begins to decrease over time. At this point where the BA concentration begins to decrease, supplemental BA can, if necessary, be delivered to the lung to maintain a therapeutic amount of the BA in the lung.

The steady state BA delivery method of the present invention includes adding to a delivery system a BA and a breathable liquid. The breathable liquid that is added is preferably substantially equal in volume to an initial filling volume of the lung (or lungs if both lungs are to be treated). The delivery system for the steady state BA delivery method is substantially similar to the delivery system for the transient BA delivery method.

Initially, the BA is introduced into the delivery system, preferably by injection from a BA injector. The BA injector site can be close to or directly into the system liquid reservoir in order to optimize homogeneity of the BA within the circulating and delivered breathable liquid volume. The BA and the breathable liquid are mixed in the delivery system to create a substantially homogeneous therapeutic mixture. This mixing preferably is conducted in the reservoir of the delivery system by sonication, ultrasound, vibration, or another similar method. Alternatively the mixing can be conducted in other components of the delivery system such as in the piping network. The patient's lung is then filled with the therapeutic mixture via the delivery system.

After the lung is filled with the therapeutic mixture, a steady state ventilation is established. The steady state ventilation has ventilatory parameters substantially similar to or the same as the baseline ventilation pattern in the transient delivery method. The therapeutic mixture is then circulated through the lung and the delivery system. During this circulation, additional BA is added to the delivery system to maintain a substantially stable concentration of the BA in the lung. The BA is added to offset the loss (e.g., consumption, excretion) of the BA in the system. The loss is computed based on the pharmacokinetics of the BA being administered.

The steady state BA delivery method is preferably automated. For example, the steps of the method can be controlled by a servo-control unit. The servo-control unit can control the flow of the therapeutic mixture, calculate the amount of BA that must be added to maintain a stable concentration of the BA in the therapeutic mixture, inject the calculated amount of BA into the delivery system at a calculated time, and control the steady state ventilation.

Advantages of the steady state BA delivery method include eliminating peaks and troughs of BA administration; and providing a stable concentration of the BA in the breathable liquid, and more importantly in the tissues of the lung. The steady state BA delivery method is preferred over the transient BA delivery method for therapies such as long term chemotherapeutic cancer treatments.

Figure 5A:
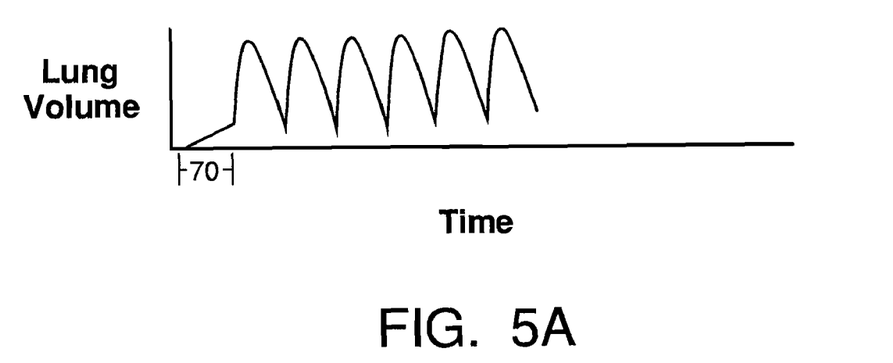
FIG. 5A is a graph showing lung volume over time during the practice of a method for steady state delivery of a biological agent in a breathable liquid.

FIG. 5A shows a patient's lung volume versus time during the practice of the steady state BA delivery method. As shown, the steady state ventilation pattern is established during the time interval represented by 70. This pattern is then substantially maintained during the practice of the steady state BA delivery method. The result is a lung volume that maintains a cyclical volume that corresponds to the stages of inspiration and expiration.

Figure 5B:
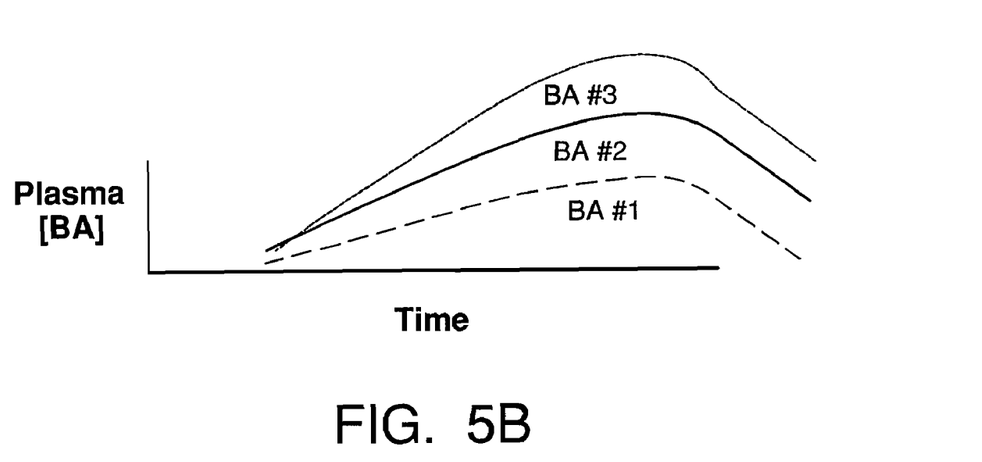
FIG. 5B is a graph showing the effect the injection concentration of the biological agent has on the concentration of the biological agent in the plasma.

FIG. 5B shows the effect the quantity of BA injected has on the concentration of the BA in the breathable liquid that is delivered to the patient's lung. The graph compares the concentration of the BA with regards to injection of BA #1, injection of BA #2 and injection of BA #3. The concentration measurements were made as if the injections were made in isolation of one another. The quantity of BA #1 injected is less than the quantity of BA #2 injected, which is less than the quantity of BA #3 injected. As a result, the concentration of BA #1 in the BA in the breathable liquid is less than the concentration of BA #2 in the breathable liquid, which is less than the concentration of BA #3 in the breathable liquid. After a steady increase, the concentrations of BA #1, BA #2, and BA #3 all begin to decrease over time. At the point where the BA concentration begins to decrease, additional BA is added to the delivery system to maintain a stable concentration of the BA in the breathable liquid. Typically, the rate of consumption of the BA is based on the half life of the BA. For example, if the initial dose of BA is 5 ml/kg and is delivered into a lung volume of 20 ml/kg with the assumption that 40% of the initial BA does remains in the body after 8 hours, then the supplemental requirements would require continuous infusion into the system of 2 ml/kg at the rate of 5 mg/20 ml over 30 minutes.

Supplemental delivery of the BA can be utilized with the steady state BA delivery method. The supplemental BA can be added to the delivery system when, for example, a spike in the BA concentration is desirable. The supplemental BA can be delivered to the delivery system by a supplemental BA delivery method that is the same as described in relation to the transient BA delivery method.

The methods of the present invention can also include an initial step of pretreating the patient's lungs with a surfactant. Surfactant pretreatment reduces collapsing pressures in the PFC-treated lung by further decreasing tension at the PFC-lung interface. Surfactant pretreatment may also confer a cytoprotective benefit to the lung, either by serving as a mechanical barrier or by direct cytoprotective action. In this regard, there can be a reduction in the number of, as well as amount of mediators released by, pulmonary inflammatory cells. Mechanisms for cytoprotection, although not elucidated, may be related to the mechanical reduction of intercellular surface tension, PFC miscibility in lipid membranes, cellular PFC ingestion, as well as PFC effect on intercellular adhesions molecules. As such, methods of the present invention can provide both mechanical and anti-inflammatory protection to an immature and/or injured lung.

When the methods of the present invention are used with PLV, the PFC liquid and the suspended BA can be instilled in the lungs for brief periods (3-5 minutes) of tidal liquid ventilation, rapid instillation of a bolus (up to 30 ml/kg) of oxygenated PFC with the ventilator disconnected can be performed. Also, PLV can include a slow infusion of oxygenated to room air equilibrated PFC in doses (up to 30 ml/kg) during continuous gas ventilation across a range of breathing frequencies in a variety of large and small animal preparations with acute RDS, aspiration syndromes as well as lung hypoplasia due to congenital diaphragmatic hernia.

The methods of the present invention can be used in the treatment of neonatal respiratory distress syndrome (NRDS), adult respiratory distress syndrome (ARDS), and chronic lung disease such bronchopulmonary dysplasia (BPD), asthma, and chronic obstructive pulmonary disease (COPD), alone or in combination with pulmonary bronchoactive drugs, decompression sickness, home ventilator care, and out patient delivery of biological agents to the lungs.

It will be appreciated by those skilled in the art that the present invention may be practiced in various alternate forms and configurations. The previously detailed description of the disclosed embodiments is presented for purposes of clarity of understanding only, and no unnecessary limitations should be implied therefrom.

We claim:

1. A method of delivering a biological agent in a breathable liquid to a lung of a patient via a liquid ventilation system comprising a ventilator circuit, the method comprising the steps of:

mixing the biological agent with a breathable liquid substantially equal in volume to an initial filling volume of the lung to create a substantially homogeneous therapeutic mixture;

filling the lung with the therapeutic mixture;

establishing a steady state ventilation that circulates the therapeutic mixture in the lung and the ventilator circuit; and adding additional biological agent to the ventilator circuit to maintain a substantially stable concentration of the biological agent in the lung.

2. The method according to claim 1, wherein ventilator circuit comprises a reservoir capable of holding the therapeutic mixture and a piping network capable of delivering the therapeutic mixture to the lung of the patient.

3. The method according to claim 1, wherein the mixing is performed by one or more of sonication, ultrasound, and vibration.

4. The method according to claim 1, wherein the biological agent is selected from the group consisting of an antibody-linked radionuclide, a vasoconstrictor, a vasodilator, a bronchoconstrictor, a bronchodilator, an anti-cancer agent, a surfactant, a steroid, an antibiotic agent, a chemotactic agent, a chemotherapeutic agent, a contrast agent, an antioxidant and an antiprotease, or a combination thereof.

5. The method according to claim 1, wherein the steady state ventilation comprises a tidal volume from about 10 to about 20 ml/kg.

6. The method according to claim 1, wherein the steady state ventilation comprises an inspiratory time from about 3 to about 7 seconds.

7. The method according to claim 1, wherein the steady state ventilation comprises an expiratory time from about 8 to about 15 seconds.

8. The method according to claim 1, wherein the steady state ventilation comprises an inspiratory:expiratory timing ratio value from about 1:2 to about 1:1.

9. The method according to claim 1, wherein the steady state ventilation comprises a breathing rate from about 3 to about 8 breaths per minute.

10. The method according to claim 1, wherein the steady state ventilation comprises an inspiratory flow rate from about 200 to about 280 ml/sec/kg.

11. The method according to claim 1, wherein the steady state ventilation comprises an expiratory flow rate from about 20 to about 60 ml/sec/kg.

12. The method according to claim 1, wherein the steady state ventilation comprises an inspiratory alveolar pressure of about 10 cmH$_2$O.

13. The method according to claim 1, wherein the steady state ventilation comprises an expiratory alveolar pressure of about 3 cmH$_2$O.

14. The method according to claim 1, wherein a servo-control unit controls timing of the steps of the method.

15. The method according to claim 14, wherein the servo control unit performs one or more of controlling flow of the therapeutic mixture, calculating the amount of biological agent that must be added to maintain a substantially stable concentration of the biological agent in the therapeutic mixture in the system, injecting the calculated amount of the biological agent into the system, and controlling the steady state ventilation.

16. The method according to claim 1, wherein the biological agent is introduced, to the liquid ventilation system by injection.

17. The method according to claim 1, further comprising calculating the amount of biological agent that must be added to maintain the substantially stable concentration of the biological agent in the lung.

18. A servo-controlled method of delivering a biological agent in a breathable liquid to a lung of a patient via a liquid ventilation system comprising a ventilator circuit comprising a piping network, the method comprising the steps of:
   mixing, the biological agent with a breathable liquid substantially equal in volume to an initial filling volume of the lung to create a substantially homogeneous therapeutic mixture;
   passing the therapeutic mixture through the piping network to till the lung with the therapeutic mixture;
   establishing a steady state ventilation that circulates the therapeutic mixture in the lung and the ventilator circuit, the steady state ventilation comprising:
      a tidal volume from about 10 to about 20 ml/kg,
      an inspiratory time from about 3 to about 7 seconds,
      an expiratory time from about 8 to about 15 seconds,
      an inspiratory:expiratory timing ratio value from about 1:2 to about 1:3,
      a breathing rate from about 3 to about 8 breaths per minute,
      an inspiratory flow rate from about 200 to about 280 rill/sec/kg, and
      an expiratory flow rate from about 20 to about 60 ml/sec/kg; and adding additional biological agent to the ventilator circuit to maintain a substantially stable concentration of the biological agent in the lung.

19. The method according to claim 18, wherein the biological agent is selected from the group consisting of an antibody-linked radionuclide, a vasoconstrictor, a vasodilator, a bronchoconstrictor, a bronchodilator, an anti-cancer agent, a surfactant, a steroid, an antibiotic agent, a chemotactic agent, a chemotherapeutic agent, a contrast agent, an antioxidant and an antiprotease, or a combination thereof.

* * * * *